US010555696B2

(12) United States Patent
Breteau et al.

(10) Patent No.: US 10,555,696 B2
(45) Date of Patent: Feb. 11, 2020

(54) DEVICE FOR MAINTAINING A USER'S VEIN IN POSITION AND DEVICE FOR PUNCTURING OR INJECTING INTO A USER'S VEIN

(71) Applicant: BEE HEALTHCARE, Nantes (FR)

(72) Inventors: Aliaume Breteau, Paris (FR); Adrien Balp, Paris (FR); Pauline Guyot, Paris (FR); Arnaud Navarro, Paris (FR); Maxime Sabouret, Paris (FR)

(73) Assignee: BEE HEALTHCARE, Nantes (FR)

( * ) Notice: Subject to any disclaimer, the term of this patent is extended or adjusted under 35 U.S.C. 154(b) by 319 days.

(21) Appl. No.: 15/303,799

(22) PCT Filed: Mar. 31, 2015

(86) PCT No.: PCT/FR2015/050842
§ 371 (c)(1),
(2) Date: Oct. 13, 2016

(87) PCT Pub. No.: WO2015/158978
PCT Pub. Date: Oct. 22, 2015

(65) Prior Publication Data
US 2017/0035335 A1    Feb. 9, 2017

(30) Foreign Application Priority Data

Apr. 14, 2014   (FR) ..................... 14 00893

(51) Int. Cl.
*A61B 5/15*      (2006.01)
*A61M 5/42*      (2006.01)
(Continued)

(52) U.S. Cl.
CPC ...... *A61B 5/150122* (2013.01); *A61B 5/0077* (2013.01); *A61B 5/15003* (2013.01);
(Continued)

(58) Field of Classification Search
CPC ..... A61B 5/489; A61B 5/4887; A61B 5/4893; A61B 5/4896; A61B 5/0077;
(Continued)

(56) References Cited

U.S. PATENT DOCUMENTS 2,525,398 A   10/1950  Collins
3,324,854 A   6/1967   Weese
(Continued)

FOREIGN PATENT DOCUMENTS

| DE | 41 15 515 A1 | 8/1992 |
| DE | 10 2005 028263 A1 | 12/2006 |
| EP | 2 289 578 A1 | 3/2011 |
| JP | 2003 310578 A | 11/2003 |

*Primary Examiner* — Nathan R Price
*Assistant Examiner* — Anh Bui
(74) *Attorney, Agent, or Firm* — Steven M. Greenberg, Esq.; Shutts & Bowen LLP

(57) ABSTRACT

A device to maintain a user's vein in position includes at least two branches separated by a gap of width greater than the size of the vein. A positioner to position the branches around the vein. The device can additionally includes a heater to heat at least one branch and a controller to control the heater. The device can further include a cooler to cool at least one branch and the controller is configured to activate the cooler.

14 Claims, 6 Drawing Sheets

(51) Int. Cl.
*A61B 5/00* (2006.01)
*A61M 5/44* (2006.01)
*A61B 5/153* (2006.01)
*A61B 8/08* (2006.01)
*A61B 17/132* (2006.01)

(52) U.S. Cl.
CPC .......... *A61B 5/153* (2013.01); *A61B 5/15016* (2013.01); *A61B 5/150129* (2013.01); *A61B 5/150748* (2013.01); *A61B 5/489* (2013.01); *A61B 5/4887* (2013.01); *A61B 8/085* (2013.01); *A61B 17/132* (2013.01); *A61M 5/42* (2013.01); *A61M 5/425* (2013.01); *A61M 5/427* (2013.01); *A61M 5/44* (2013.01); *A61B 5/4893* (2013.01); *A61B 5/4896* (2013.01)

(58) Field of Classification Search
CPC .. A61B 5/150748; A61B 8/085; A61M 5/427; A61M 5/42; A61M 5/425
See application file for complete search history.

(56) References Cited

U.S. PATENT DOCUMENTS

| | | | |
|---|---|---|---|
| 8,888,714 B1* | 11/2014 | Soto | A61B 5/1535 600/573 |
| 2002/0042589 A1* | 4/2002 | Marsoner | A61M 5/46 604/46 |
| 2005/0257795 A1* | 11/2005 | Hsiu-Chen | A61B 5/489 128/898 |
| 2006/0129184 A1* | 6/2006 | Peters | A61B 17/1322 606/201 |
| 2008/0021329 A1* | 1/2008 | Wood | A61B 5/0059 600/476 |
| 2008/0221519 A1* | 9/2008 | Schwach | A61B 5/0059 604/116 |
| 2010/0268130 A1* | 10/2010 | Khan | A61H 9/0078 601/46 |
| 2011/0301500 A1* | 12/2011 | Maguire | A61B 5/489 600/583 |

* cited by examiner

DEVICE FOR MAINTAINING A USER'S VEIN IN POSITION AND DEVICE FOR PUNCTURING OR INJECTING INTO A USER'S VEIN

RELATED APPLICATIONS

This application is a § 371 application from PCT/FR2015/050842 filed Mar. 31, 2015, which claims priority from French Patent Application No. 14 00893 filed Apr. 14, 2014, each of which is incorporated herein by reference in its entirety.

TECHNICAL FIELD OF THE INVENTION

The present invention relates to a device for maintaining a user's vein in position and a device for puncturing or injection into a user's vein. It applies, in particular, to blood punctures, blood injections and the placing of catheters.

STATE OF THE ART

In hospitals, taking blood samples and placing catheters are very repetitive, time-consuming procedures for the medical staff. Involving a large proportion of the members of the medical staff, this type of procedure is the cause of frequent errors and injuries, and is an additional financial cost for the hospital.

Each day, millions of injections are given worldwide. Each year, several million injuries caused by badly-placed injections are reported, and in addition it is estimated that 55% of errors are not reported. Many practitioners are also injured by the needles and infected with the patient's germs, leading in some cases to serious medical complications.

Furthermore, the risk for a health professional of contamination from a patient suffering from a disease such as AIDS (HIV virus), for example, increases the danger linked to treating these patients.

Also, current systems do not make it possible to reduce patients fear of needles, nor the pain caused by the cutaneous insertion of this needle.

OBJECT AND SUMMARY OF THE INVENTION

The present invention aims to remedy all or part of these drawbacks.

To this end, according to a first aspect, the present invention envisages a device for maintaining a user's vein in position, which comprises:

at least two branches separated by a gap of width greater than the size of the vein; and
a means for positioning the branches around the vein.

Thanks to these provisions, a vein on which a medical treatment is to be dispensed is maintained in position by the branches of the device.

In some embodiments, the device that is the subject of the present invention comprises:

a means for heating at least one branch; and
a means for controlling the heating means.

These embodiments have the advantage of making it possible to dilate the vein on which treatment is to be dispensed.

In some embodiments, the device that is the subject of the present invention comprises a means for cooling at least one branch, the control means being configured to activate the cooling means after activation of the heating means.

The advantage of these embodiments is that they make it possible, for example thanks to the use of a Peltier effect, to anesthetize an area of the user's body around the vein on which treatment is to be dispensed. As the sensation of cold passes through the nervous system faster than the sensation of pain, the user feels the cold instead of the sensation of pain.

In some embodiments, the device that is the subject of the present invention comprises a means for emitting ultraviolet light in the direction of the user's vein.

These embodiments have the advantage of sterilizing the skin around the vein, and also any medical equipment around this area.

In some embodiments, the device that is the subject of the present invention comprises a means for disinfecting the skin covering the user's vein.

The advantage of these embodiments is that they make it possible to avoid the risk of infection for the user during a medical procedure performed on the vein to be treated.

In some embodiments, the positioning means comprises a means for pinching the vein by the branches.

These embodiments have the advantage of making it possible to maintain the vein in position and to increase the area of contact between the branches and the user's skin.

According to a second aspect, the present invention envisages a device for puncturing or injecting into a user's vein, which comprises:

a device for maintaining a user's vein in position that is the subject of the present invention; and
an opaque casing comprising an opening to receive the user's arm.

Thanks to these provisions, sight of a treatment being dispensed on the vein is hidden from this user so as to avoid the user feeling fear, for example.

In some embodiments, the puncturing or injection device that is the subject of the present invention comprises:

a means for capturing an infrared image of the arm received in the casing;
a means for detecting a vein in the image detected;
a means for transmitting a location of the vein detected, the means for positioning branches around the vein being controlled according to the location of the vein.

These embodiments enable the positioning of the branches to be performed automatically.

In some embodiments, the puncturing or injection device that is the subject of the present invention comprises:

a needle; and
a means for positioning an extremity of the needle in the vein detected, between the branches.

The advantage of these embodiments is that they make it possible to insert the needle into the vein detected so as to dispense a treatment on the vein.

In some embodiments, the puncturing or injection device that is the subject of the present invention comprises:

a means for emitting ultrasound; and
a means for capturing an image as a function of the ultrasounds emitted,
the positioning means positioning the needle as a function of the image captured.

These embodiments have the advantage of not being sensitive to an emission of heat by a branch that may interfere with the detection of the vein.

In some embodiments, the puncturing or injection device that is the subject of the present invention comprises a means for switching between a needle that has performed a puncture and/or an injection and another needle.

The advantage of these embodiments is that they make it possible to automate the change of needles occurring between two treatments dispensed by the device.

In some embodiments, the puncturing or injection device that is the subject of the present invention comprises a means for maintaining the arm of the user in the casing.

These embodiments have the advantage of reducing the risks of injury that might result from an unexpected withdrawal of the user's arm.

In some embodiments, the maintenance means comprises a tourniquet contracting automatically around the user's arm and a handle to receive the user's closed hand.

The advantage of these embodiments is that they enable the arm to be maintained at two points, improving its stability.

In some embodiments, the puncturing or injection device that is the subject of the present invention comprises:
- a means for aspirating blood from the vein in which the needle is positioned; and
- a removable reservoir for receiving the blood aspirated.

These embodiments have the advantage of making it possible to automate a puncture type of treatment dispensed on the vein.

In some embodiments, the puncturing or injection device that is the subject of the present invention comprises:
- a means for accessing a profile of the user;
- a means for identifying the reservoir with an item of data of the user's profile.

The advantage of these embodiments is that they make it possible to identify a reservoir according to the item of user profile data.

BRIEF DESCRIPTION OF THE FIGURES

Other particular advantages, aims and features of the invention will become apparent from the non-limiting description that follows of at least one particular embodiment of the device for maintaining a user's vein in position and the device for puncturing or injecting into a user's vein that are the subjects of the present invention, with reference to drawings included in an appendix, wherein.

DETAILED DESCRIPTION OF THE EMBODIMENTS

The present description is given as a non-limiting example, each characteristic of an embodiment being able to be combined with any other characteristic of any other embodiment in an advantageous way. In addition, each parameter of an example of realization can be utilized independently from the other parameters of said example of realization.

It is noted that the terms "one, a; an" are used in the sense of "at least one".

It is now noted that the figures are not to scale.

It is noted that the computerized processing performed are, for example, performed by a Raspberry Pi (registered trademark) type of minicomputer.

Figure 1:
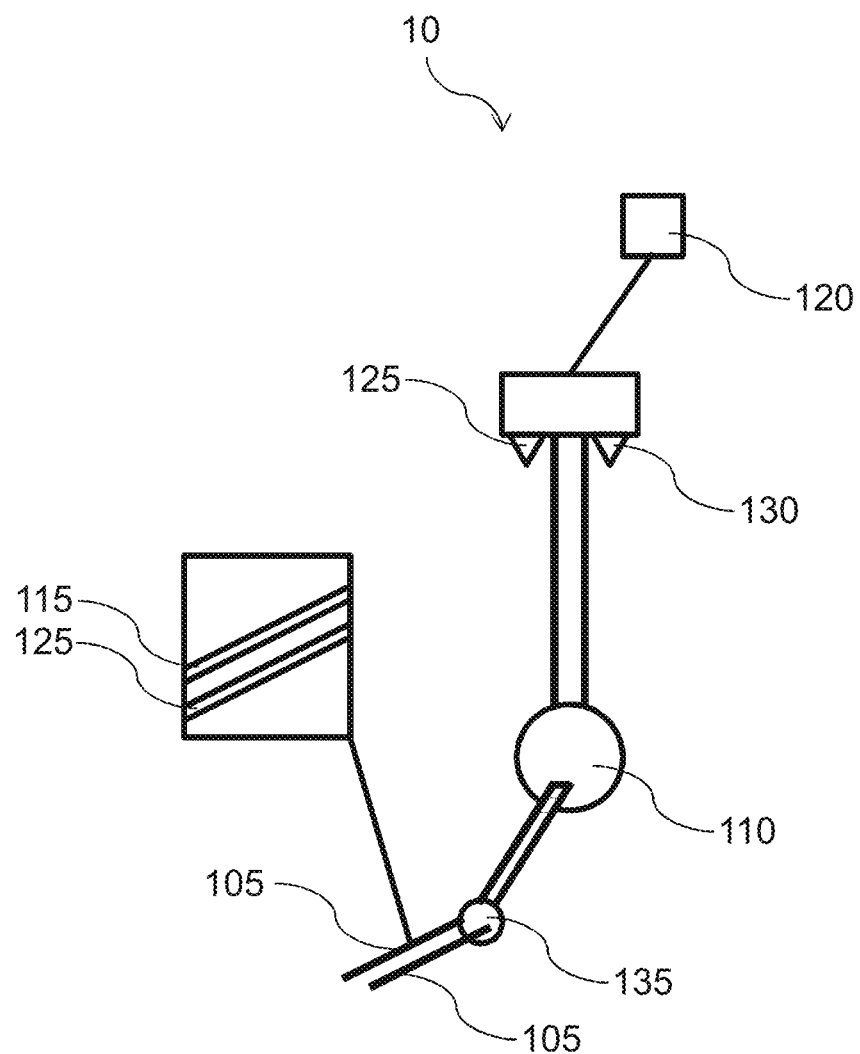
FIG. 1 represents, schematically and in cross-section, a particular embodiment of the maintenance device that is the subject of the present invention.

FIG. 1, which is not to scale, shows a cross-section view of an embodiment of the device 10 for maintaining a user's vein in position that is the subject of the present invention. This device 10 comprises:
- at least two branches 105 separated by a gap of width greater than the size of the vein; and
- a means 110 for positioning the branches 105 around the vein, comprising a means 135 for pinching the vein by the branches 105;
- a means 115 for heating at least one branch 105;
- a means 125 for cooling at least one branch 105;
- a means 120 for controlling the heating means 115 and the cooling means 125;
- a means 125 for emitting ultraviolet light in the direction of the user's vein; and
- a means 130 for disinfecting the skin covering the user's vein.

The two branches 105 are, for example, parallel metal strips separated by a gap one centimeter wide. These strips can be made of any type of rigid material, such as plastic, ceramic or glass, for example.

In some preferred variants, each branch 105 is configured to produce a Peltier effect. These branches 105 therefore comprise two surfaces, made of electro-insulating ceramic for example, separated by semiconductors acting as contacts between two electrical conductors, each positioned on one surface. In some variants, some semiconductors are P-type doped and other semiconductors are N-type doped. Applying a current in one of the electrical conductors results in heat being emitted by one of the surfaces and heat being absorbed by the other surface. In these variants, any existing type of Peltier cell known to the person skilled in the art can be used.

These branches 105 are positioned by the positioning means 110. This positioning means 110 is, for example, an arm configured to move in translation along three axes a means for rotating the branches 105. This means for rotating the branches 105 comprises a means for locking the position such that the branches 105 are constrained from moving once the positioning has been carried out.

This means for rotating the branches 105 is associated to a means 135 for pinching the vein by the branches 105. This pinching means 135 is, for example, a motor configured to bring the branches 105 closer together so as to pinch a user's skin. The positioning means 110 can be motorized or not.

In some variants, the positioning means 110 is mounted on a base and articulated so that a user positions the positioning means 110 by the movement in space of a head comprising the branches 105.

The heating means 115 is, for example, an assembly formed by two similarly-oriented surfaces of the branches 105. These two surfaces are, for example, similar surfaces of Peltier cells as described above. These two surfaces are configured to emit heat jointly or independently.

The cooling means 125 is, for example, an assembly formed by the other two surfaces of the branches 105. These other two surfaces have similar orientations. These two surfaces are, for example, similar surfaces of Peltier cells as described above. These two surfaces are configured to absorb heat jointly or independently.

In some variants, the device 10 comprises a means for rotating the branches 105 so as to, first, heat a portion of a user's skin around the vein to be treated, and then to cool the same portion.

Activation of the heating means 115 and of the cooling means 125 is controlled by the control means 120. This control means 120 is, for example, a printed circuit comprising a microcontroller. This microcontroller is configured to control the transmission of an electrical current to each Peltier cell.

The control means 120 is configured to activate the cooling means 125 after activation of the heating means 115.

In some variants, the control means 120 is controlled by a button of the device 10 being activated by a user.

The means 125 for emitting an ultraviolet light is, for example, an ultraviolet lamp or a plurality of ultraviolet lamps. Each lamp is configured to be activated by a microcontroller of the printed circuit. The activation of each lamp can be automatic and performed when the positioning means 110 is locked.

In some variants, each lamp is activated by a button of the device 10 being activated by a user.

The disinfection means 130 is, for example, a sprayer of a disinfectant liquid. In some variants, this disinfection means 130 is a brush connected to a motorized arm configured to scrub the user's arm with the brush. This motorized arm is activated, for example, by a microcontroller of the printed circuit.

Figure 2:
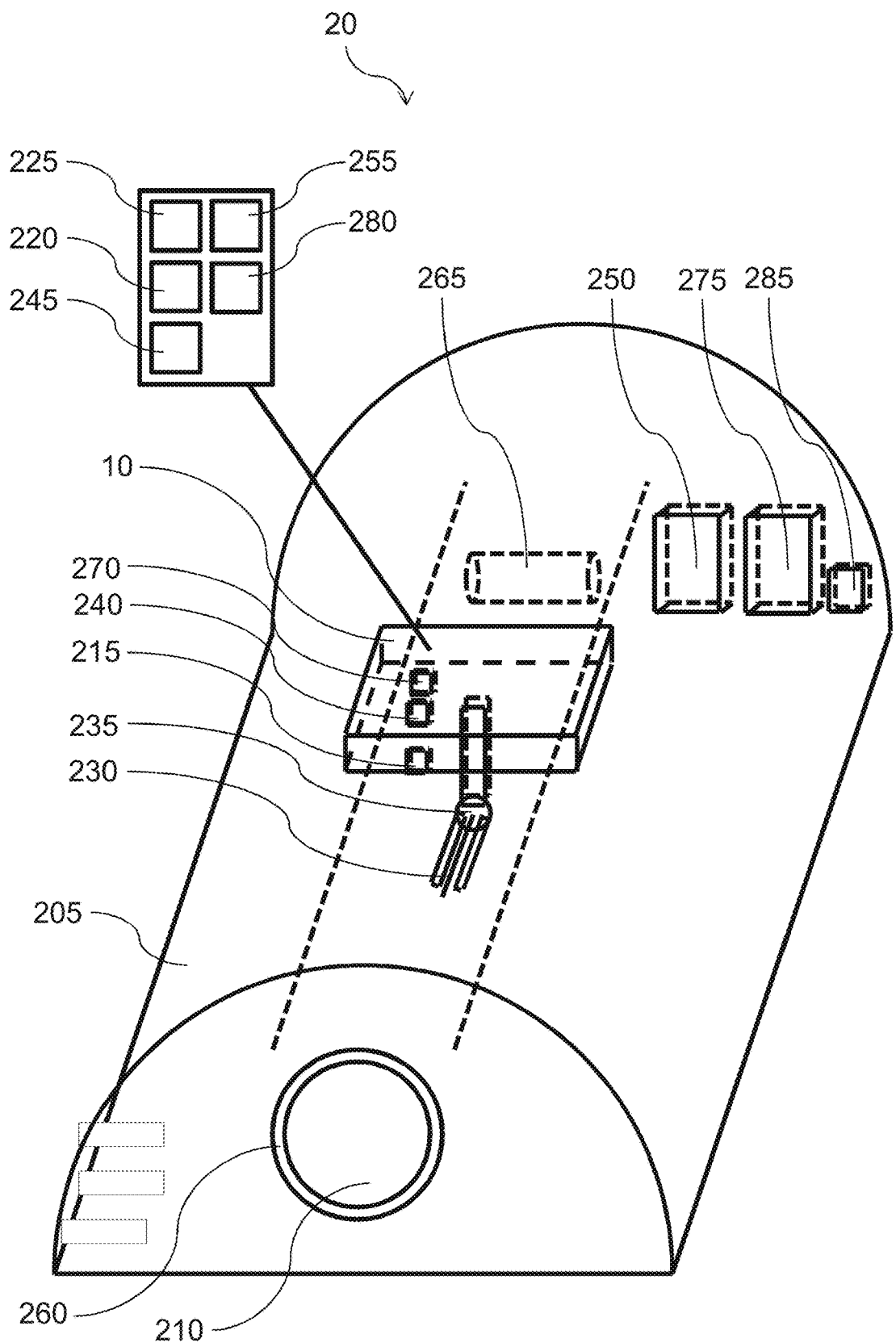
FIG. 2 represents, schematically and in cross section, a first particular embodiment of the puncturing or injection device that is the subject of the present invention.

FIG. 2, which is not to scale, shows a view of a first embodiment of the device 20 for puncturing or injecting into a user's vein that is the subject of the present invention. This device 20 comprises:
- a device 10 for maintaining a users vein in position;
- an opaque casing 205 comprising an opening 210 to receive the users arm;
- a means 215 for capturing an infrared image of the arm received in the casing 205;
- a means 220 for detecting a vein in the image detected;
- a means 225 for transmitting a location of the vein detected,
- the means 110 for positioning branches 105 around the vein being controlled according to the location of the vein;
- a needle 230;
- a means 235 for positioning an extremity of the needle in the vein detected, between the branches 105;
- a means 240 for emitting ultrasound;
- a means 245 for capturing an image as a function of the ultrasounds emitted;
- a means 250 for switching between a needle 230 that has performed a puncture and/or an injection and another needle;
- a means 255 for maintaining the arm of the user in the casing, which comprises:
  - a tourniquet 260 contracting automatically around the user's arm; and
  - a handle 265 to receive the user's closed hand;
- a means 270 for aspirating blood from the vein in which the needle 230 is positioned;
- a removable reservoir 275 for receiving the blood aspirated;
- a means 280 for accessing a profile of the user;
- a means 285 for identifying the reservoir 275 with an item of data of the user's profile.

The device 10 is similar to the device 10 described in FIG. 1. This device 10 is positioned in an opaque casing 205. This casing 205 is, for example, a structure in the shape of a half-cylinder of rotation comprising an opening 210 on one of the flat surfaces. This opening 210 is configured to receive a user's arm and can be of any geometric shape.

In order for the positioning means 110 of the device 10 to be moved, the device 10 is fixed to two rails traversing the casing 205 longitudinally. These rails each comprise a rack along which the device 10 moves. A second rack, oriented along an axis orthogonal to the two longitudinal rails, makes it possible to position the device 10 along a transverse axis of the casing 205. A third rack oriented along a vertical axis orthogonal to the other two axes of the first and second racks makes it possible to position the device 10 at height. The positioning of the device 10 can be performed by using a set of stepping motors.

In some variants, the positioning of the device 10 is performed by a robotized arm comprising two articulations.

The means 215 for capturing an infrared image of the arm received in the casing 205 is, for example, an infrared camera configured to capture an image in the infrared spectrum. This capture means 215 is positioned on the mobile device 10 and oriented towards the user's arm. In some variants, the capture means 215 is positioned on a module moving along the longitudinal racks. In these variants the device 10 can be immobile along said racks and positioned at the end of the longitudinal rails.

In some variants, the capture means 215 is associated to a polarizer.

The means 220 for detecting a vein in the image detected is, for example, a computer program embedded in a component of the printed circuit of the device 10. This component is connected to the capture means 215 such that the captured image is transferred to the detection means 220. By processing the image, for example by edge detection, this computer program determines the arrangement of the veins along the user's arm. This detection means 220 selects a vein amongst the veins detected according to the width of the vein detected. Preferably, the widest vein is selected.

In some variants, the computer program utilizes grayscale conversion, contrast enhancement, adaptive thresholding and then edge detection.

In some variants, a plurality of light-emitting diodes, organized in a ring, illuminates the arm.

The ultrasound emission means 240 is, for example, an ultrasound emitter positioned near the device 10 and configured to emit ultrasounds towards the user's arm. This emission means 240 receives an ultrasound emission command emitted by a component of the printed circuit of the device 10. This command is emitted once a vein has been detected by the detection means 220.

The means 245 for capturing an image according to the ultrasounds emitted is, for example, an ultrasound sensor. This ultrasound sensor makes it possible, in particular, to detect the depth of a vein detected by the detection means 220. If the detected depth is greater than a predefined limit value, the detection means 220 selects another vein and the ultrasound emission means 240 is utilized again.

In some variants, the emission means 240 and the capture means 245 are replaced by an ultrasound emission means in the needle 230 and a sensor of the resonance frequency of the needle 230 according to the ultrasound signal emitted. In the air, the needle has a specific resonance frequency, which varies slightly when said needle is inserted into the user's skin. The resonance frequency varies abruptly when the needle penetrates a vein, which indicates to the device that a vein has been pierced. In some variants, every type of ultrasonic imagery device can be used.

In some variants, the device 20 comprises a means for detecting the penetration of the needle 230 into a vein. This detection means is, for example, a piezoelectric crystal configured to emit an electrical signal as a function of a spontaneous low-amplitude variation in the longitudinal position of the needle 230, this variation corresponding to the needle 230 piercing a wall of the vein.

In some variants, the device 20 comprises a means for detecting the depth of a detected vein. This detection means detects the depth of a vein by scanning the user's arm with a 3D sensor. 3D imaging, associated with infrared imaging, makes it possible to select the user's vein.

The means 110 for positioning branches 105 around the vein is, for example, the positioning means 110 of device 10 described in FIG. 1. This positioning means 110 is controlled by a microcontroller of the device 10. This microcontroller is configured to position the positioning means 110 according to the location of the vein detected. The device 10 is positioned such that the branches 105 pinch the skin at the location of the vein detected.

In some variants, the device 20 comprises a means for verifying the maintenance of the vein. This verification means is a component of the electronic circuit of the device 10 configured to command the capture means 215 and detection means 220 to perform a new vein detection. If the vein detected is not maintained, the positioning of the branches 105 is performed again.

The device 20 comprises a needle 230. This needle 230 is, for example, positioned in a needle mount 230 attached to the positioning means 110. In some variants, this needle 230 is parallel to the branches 105 and initially retracted between the branches. When an insertion of the needle 230 into the user's skin is performed, the needle 230 is pushed so as to protrude beyond the plane formed by the two branches 105.

This insertion of the needle 230 is performed by the positioning means 235. This positioning means 235 is, for example, a motor configured to move the needle 230 in translation.

In some variants, the needle 230 is configured to perform a puncture, an injection or placing of a catheter.

The means 250 for switching between a needle 230 that has performed a puncture and/or an injection and another needle is, for example, a dispenser of needles. This dispenser comprises a reservoir of sterile needles and a cavity allowing a single needle to pass at a time. Each needle slotting into the cavity is maintained by a needle mount. Once a used needle is released by the device 10 into a reservoir of used needles, a needle mount is assembled by screwing into the device 10 so as to replace the previous needle mount. This switching means 250 is positioned, for example, at one extremity of the casing 205 opposite the opening 210.

The means 255 for maintaining the arm of the user in the casing 205 is, for example, a component of the electronic circuit of the device 10 configured to activate a contraction of the tourniquet 260.

This tourniquet 260 is, for example, a pneumatic tourniquet surrounding the opening 210 and is configured to be inflated on receipt of a command emitted by the maintenance means 255. In some variants, this tourniquet 260 is a wire tightened by the activation of a motor leading to a reduction of the wire's perimeter around the arm.

The maintenance means 255 also comprises a handle 265 to receive the user's closed hand. This handle 265 is positioned, for example, at one extremity of the casing 205 opposed in relation to the opening 210.

The means 270 for aspirating blood from the vein in which the needle 230 is positioned is, for example, a pump configured to aspirate the blood from the vein to a removable reservoir 275 for receiving the blood aspirated. This reservoir 275 is, for example, a pocket made of plastic.

The means 280 for accessing a profile of the user is, for example, a network card configured to connect to an internet or intranet type of data network and, as a function of a user identifier entered by a user, extract user data from a database. These user data can be, for example, a last name, first name, age, gender, blood type.

The means 285 for identifying the reservoir 275 with an item of data of the user's profile is, for example, an electronic circuit configured to enter the data extracted into an NFC chip associated with the reservoir. In some variants, this identification means 285 is a printer configured to print an extracted item of data onto a self-adhesive label stuck onto the reservoir 275.

In some variants, the device 20 comprises a safety button configured to cause the needle 230 to be withdrawn and the device 20 to be stopped.

Figure 3:
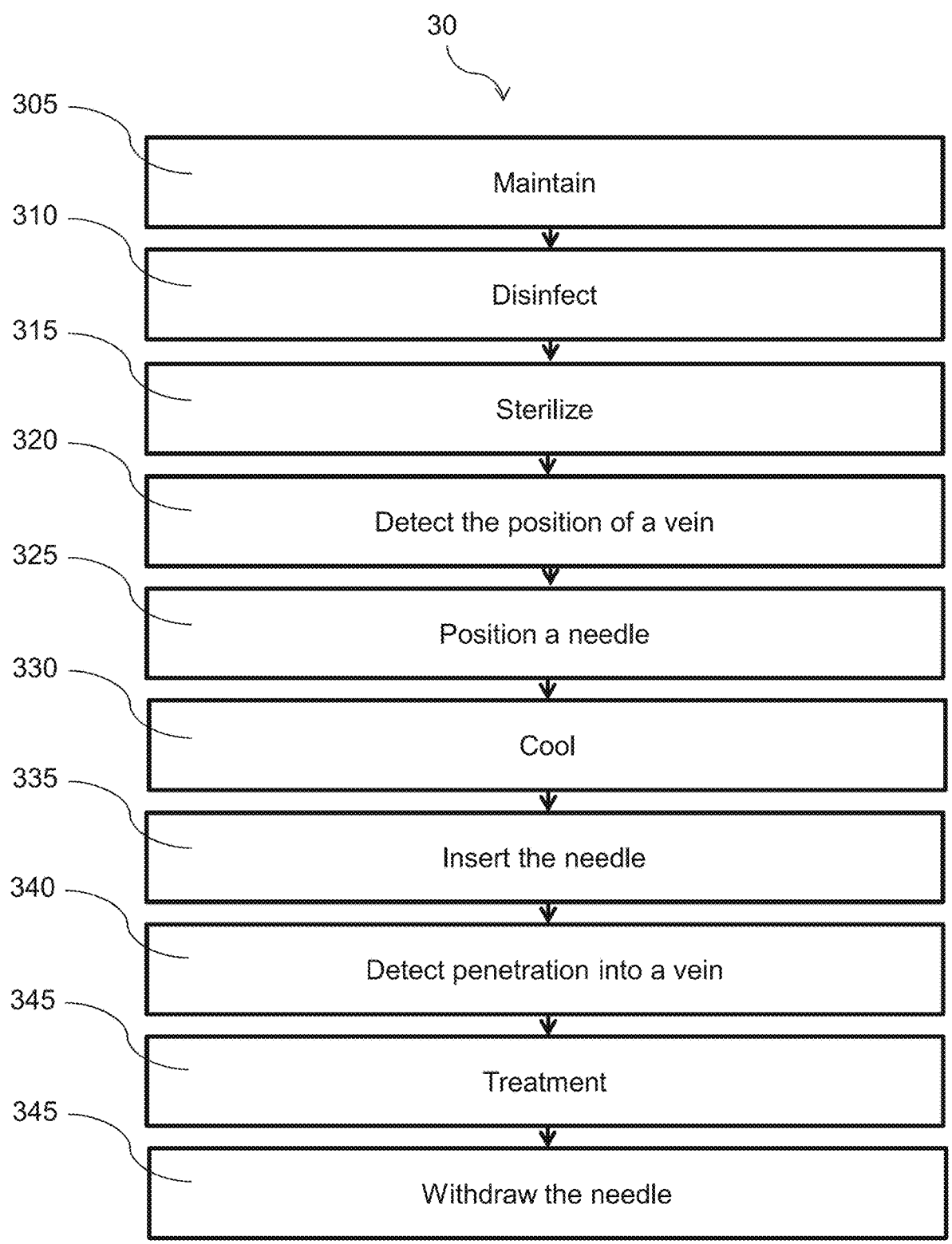
FIG. 3 represents, schematically and in cross-section, a logical diagram of particular steps of the method that is the subject of the present invention.

FIG. 3, which is not to scale, shows a cross-section view of an embodiment of the method 30 that is the subject of the present invention. This method 30 comprises:
- a step 305 of maintaining an arm of a user in the device 20;
- a step 310 of disinfecting the skin covering the vein;
- a step 315 of sterilizing the skin;
- a step 320 of detecting a vein;
- a step 325 of positioning the device for maintaining a vein;
- a step 330 of cooling the skin;
- a step 335 of inserting a needle into a vein of a user;
- a step 340 of detecting a needle's depth of penetration into a vein;
- a step 345 of dispensing a treatment on the vein; and
- a step 350 of withdrawing the needle from the vein.

The maintenance step 305 is performed, for example, by utilizing a tourniquet and a handle as described in FIG. 2. When the user has positioned an arm inside the casing of the device 20 as described in FIG. 2 and caught hold of the handle, the tourniquet is activated. This tourniquet surrounds the user's arm at the opening of the casing.

The disinfection step 310 is performed, for example, by utilizing a disinfection means as described in FIG. 2. Once the tourniquet has been activated, the disinfection means disinfects the skin of the user's arm.

The sterilization step 315 is performed, for example, by utilizing a means for emitting an ultraviolet light as described in FIG. 1. Once the disinfection means has disinfected the user's arm, an ultraviolet light is emitted so as to sterilize the environment inside the casing of the device 20.

The detection step 320 is performed, for example, by utilizing the infrared image capture means and the detection means as described in FIG. 2. During this step, a vein is detected by edge detection and then selected as a function of the detected width of the vein. In some variants, using ultrasonic imaging detection makes it possible to detect the depth of the vein.

In some variants, a user selects the vein on a screen of an external device connected to the device dispensing the treatment. Such a screen is mounted on a digital tablet, for example.

The piercing device communicates with the external device by means of a wireless technology such as Bluetooth, Wi-Fi or ZigBee.

The positioning step 325 is performed, for example, by utilizing a positioning means as described in FIG. 1. The positioning means positions the branches of the device so as to surround a detected vein of the user.

The positioning step 325 utilizes, for example:
movement of the needle towards the piercing area;
positioning of the needle above the piercing area;
piercing by the needle until the vein is pierced;
inclining the needle so that it can pass into the vein;
pushing the needle a second time so that it can pass into the vein; and
withdrawing the needle.

In some variants, a heating step is performed, for example, by utilizing a heating means as described in FIG. 1. This heating means heats the skin of the user's arm.

The cooling step 330 is performed, for example, by a cooling means as described in FIG. 1. During this step, the users arm is cooled by the cooling means.

The needle insertion step 335 is performed by activating a motor to move the needle in a vein of the user.

In some variants, the method 30 comprises a step of confirming an insertion to be performed, this step utilizing, for example, entry of a user command on a communicating portable terminal. Such a communicating portable terminal is, for example, a digital tablet. The command entry utilizes a man-machine interface, such as a touch screen, for example.

The penetration depth detection step 340 is performed, for example, by detecting ultrasounds emitted in the needle varying as a function of the needle's position. In the air, the needle has a specific resonance frequency, which varies slightly when said needle is inserted into the users skin. The resonance frequency varies abruptly when the needle penetrates a vein, which indicates to the device that a vein has been pierced. In some variants, every type of ultrasonic imagery device can be used.

The treatment dispensing step 345 is performed, for example, by a needle as described in FIG. 2. This treatment can correspond to a puncture, an injection or the placing of a catheter.

The withdrawal step 350 is performed, for example, by utilizing the positioning means as described in FIG. 1. Once the treatment has been dispensed, the needle is withdrawn from the users vein.

In some variants, the method 30 comprises a step of recording in a database an item of data representative of the nature and amount of product injected, of a volume of blood collected, or the placing of a catheter. In other variants, an item of timestamp information corresponding to the dispensing of the treatment is recorded.

The information thus recorded can be consulted before a new treatment is dispensed. Depending on this information, for example, an amount of product and/or the nature of a product to be injected is determined automatically.

Figure 4:
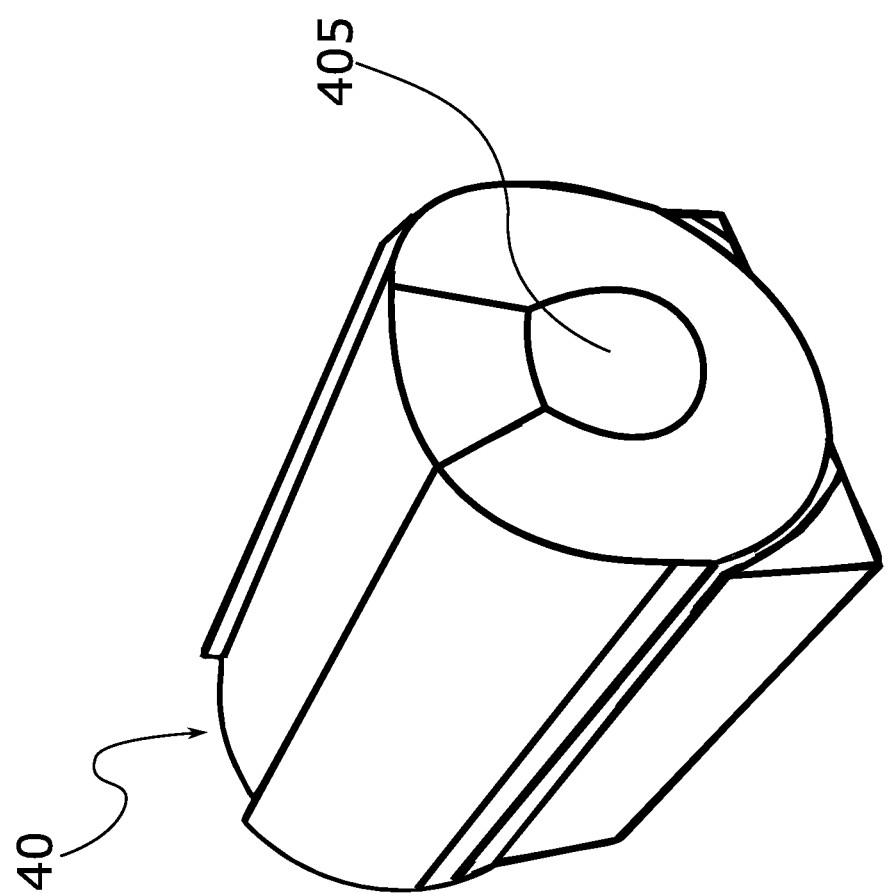
FIG. 4 represents, schematically and in cross section, a second particular embodiment of the puncturing or injection device that is the subject of the present invention.

FIG. 4 shows, schematically and in perspective, a second embodiment of the puncturing or injection device 40 that is the subject of the present invention. This device 40 has an opening 405 in a roughly cylindrical casing. The inside of this casing is similar to the device 20 that is the subject of the present invention.

Figure 5:
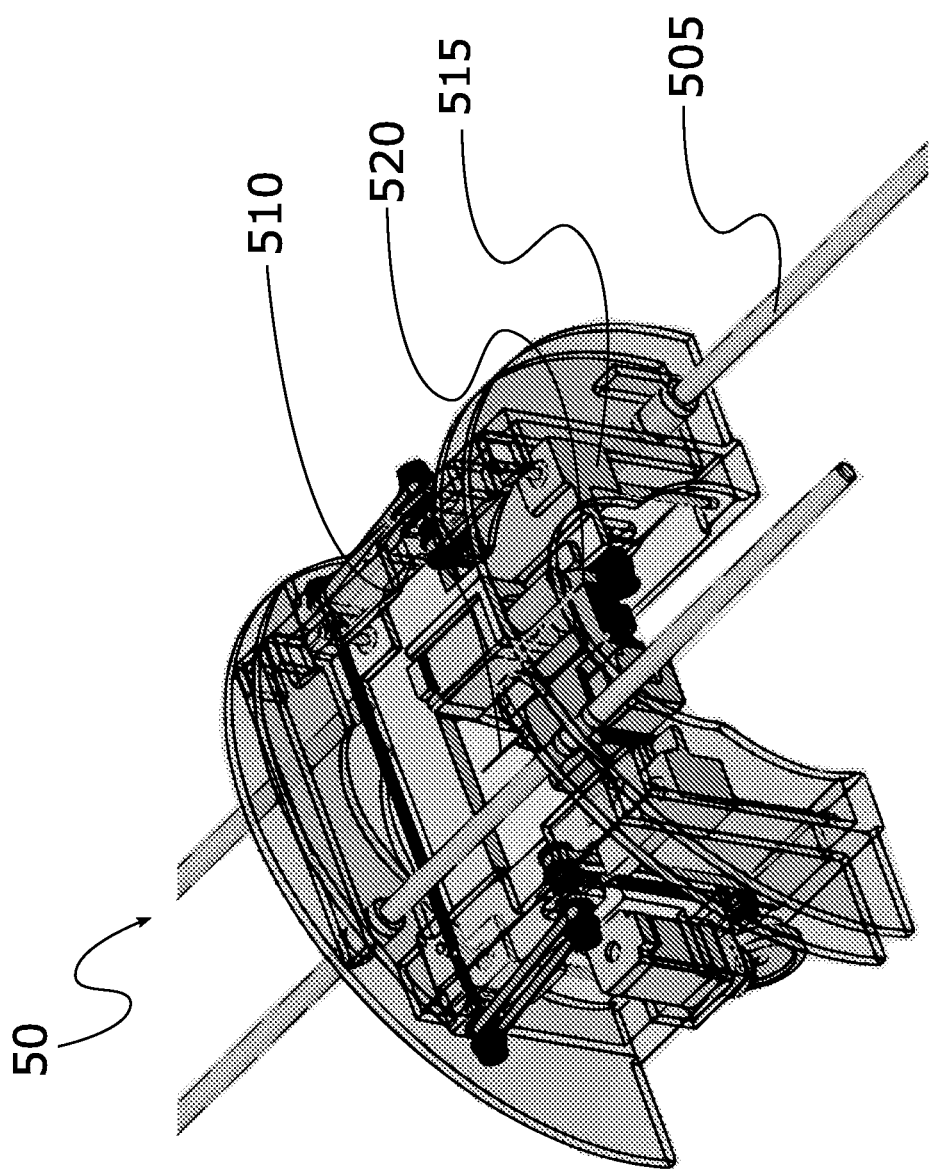
FIG. 5 represents, schematically and in cross-section, a third particular embodiment of the puncturing or injection device that is the subject of the present invention.

FIG. 5 shows, schematically and in perspective, a third embodiment of the puncturing or injection device 50 that is the subject of the present invention. This FIG. 5 shows, in particular, a rail 505 for moving a so-called "piercing" module, ie comprising a needle 510. This piercing module comprises a plate 515 moving in altitude, ie along an axis orthogonal to the axis formed by the rail 505. This piercing module also comprises a mount free in rotation comprising the needle 510.

Figure 6:
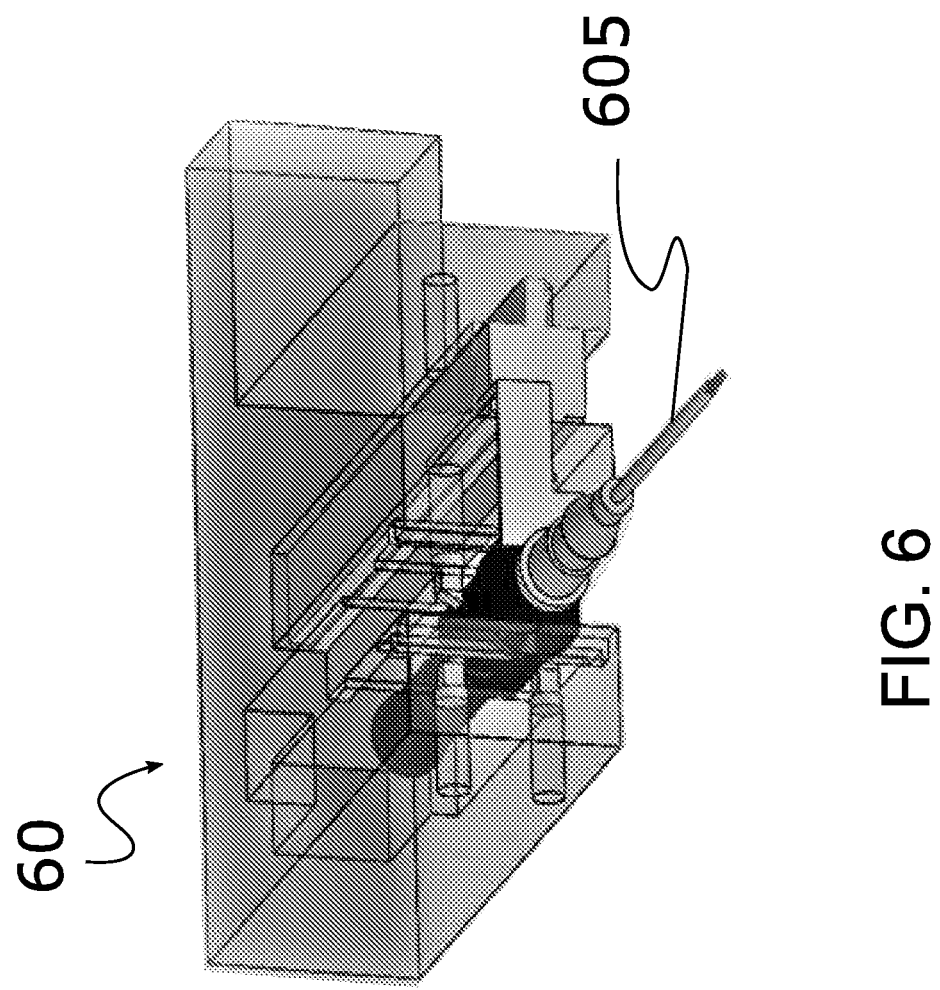
FIG. 6 represents, schematically and in cross-section, a fourth particular embodiment of the puncturing or injection device that is the subject of the present invention.

FIG. 6 shows, schematically and in perspective, a fourth embodiment of the puncturing or injection device 60 that is the subject of the present invention. This FIG. 6 shows more specifically a means for pushing the needle 605 so that this needle enters into and/or withdraws from a vein for example.

It is noted that the devices, 10, 20 and 40, as described with reference to FIG. 1, 2 or 4, can be connected in a wired or wireless way with a communicating terminal, such as a computer. This communicating terminal can also be portable, such as a smartphone or a digital tablet, for example.

These devices can also communicate with a remote computing unit, such as a server for example. The information transmitted to such a server directly, or indirectly by means of a terminal communicating with said device, can be utilized by a patient monitoring application and/or platform.

This platform and/or this application utilizes, for example:
user sessions for health-care staff;
a user-patient search;
initiation of the dispensing of a treatment by user entry;
real-time monitoring of a treatment being dispensed by
displaying information representative of the treatment in progress on a screen, for example; and/or
viewing a file for a user-patient, this file comprising data relating to this user's health.

The invention claimed is:

1. A device for puncturing or injection into a user's vein, comprising:
a device to maintain a user's vein in position, comprising at least two branches separated by a gap of width greater than a size of the user's vein, means for rotating the branches and an arm configured to move in translation along three axes, the means for rotating the branches and to position the branches around the user's vein;
a sensor to capture an infrared image of the user's arm;
a detector to detect a vein in the captured infrared image;
a transmitter to transmit a location of the detected vein;
the arm configured to position automatically the branches around the user's vein being controlled according to the location of the detected vein;
a needle; and
a motor to position an extremity of the needle in the detected vein between the branches.

2. The device according to claim 1, further comprising:
an emitter to emit ultrasounds;
a sensor to capture an image as a function of the emitted ultrasounds; and
wherein the motor is configured to position the needle as a function of the captured image as a function of the emitted ultrasounds.

3. The device according to claim 1, further comprising a switch to change between a needle that has performed at least one of a puncture and an injection, and another needle.

4. The device according to claim 1, further comprising an opaque casing comprising an opening to receive the user's arm.

5. The device according to claim 4, further comprising a maintenance circuit to maintain the user's arm in the opaque casing.

6. The device according to claim 5, wherein the maintenance circuit comprises a tourniquet configured to contract automatically around the user's arm and a handle to receive the user's closed hand.

7. The device according to claim 1, further comprising an aspirator to aspirate blood from the user's vein in which the needle is positioned; and a removable reservoir to receive the aspirated blood.

8. The device according to claim 7, further comprising an identifying circuit to identify the removable reservoir with an item of data of a user's profile extracted from a database over a communications network.

9. The device according to claim 1, wherein the device to maintain the user's vein in position further comprises a heater to heat at least one branch; and a controller to control the heater.

10. The device according to claim 1, wherein the device to maintain the user's vein in position further comprises a cooler to cool at least one branch and a controller configured to activate the cooler.

11. The device according to claim 1, wherein the device to maintain the user's vein in position further comprises an ultraviolet emitter to emit an ultraviolet light in a direction of the user's vein.

12. The device according to claim 1, wherein the device to maintain the user's vein in position further comprises a disinfector to disinfect a skin covering the user's vein.

13. The device according to claim 1, wherein the device to maintain the user's vein in position further comprises a pincher to pinch the user's vein by the branches.

14. The device according to claim 1, wherein the needle is parallel to the branches and initially retracted between the branches.

\* \* \* \* \*